US006432884B1

(12) United States Patent
Lachut

(10) Patent No.: US 6,432,884 B1
(45) Date of Patent: Aug. 13, 2002

(54) AGRICULTURAL ADJUVANT

(75) Inventor: Frank J. Lachut, West Chester, OH (US)

(73) Assignee: Cognis Corporation, Gulph Mills, PA (US)

( * ) Notice: Subject to any disclaimer, the term of this patent is extended or adjusted under 35 U.S.C. 154(b) by 462 days.

(21) Appl. No.: 09/205,530

(22) Filed: Dec. 3, 1998

Related U.S. Application Data

(63) Continuation-in-part of application No. 08/986,493, filed on Dec. 8, 1997, now abandoned.

(51) Int. Cl.[7] .......................... A01N 25/30; B01F 17/00

(52) U.S. Cl. ....................... 504/363; 504/364; 514/975; 424/405; 516/204

(58) Field of Search .................. 424/405; 514/975; 516/204; 504/363, 364

(56) References Cited

U.S. PATENT DOCUMENTS

| 4,556,410 A | 12/1985 | Ronning et al. ................ 71/78 |
| 5,084,087 A | 1/1992 | Hazen et al. .................. 71/123 |
| 5,631,205 A | 5/1997 | Killick et al. ................ 504/116 |

*Primary Examiner*—S. Mark Clardy
(74) *Attorney, Agent, or Firm*—John E. Drach; Steven J. Trzaska

(57) ABSTRACT

Compositions useful as adjuvants for agricultural chemical formulations are comprised of a lower alkanol ester of a fatty acid and an emulsifier package. The emulsifier package is comprised of a nonionic surfactant selected from the group consisting of an ethoxylated castor oil, an alkoxylated castor oil, an ethylene-propylene block copolymer, an ethoxylated-propoxylated alkyl phenol, an ethoxylated sorbitan fatty acid ester, a sorbitan fatty acid ester and an anionic surfactant selected from the group consisting of an ethoxylated partial phosphate ester, alkyl sulfate, an alkyl ether sulfate, a branched alkyl benzene sulfonate, a linear alkyl benzene sulfonate and an alpha olefin sulfonate. The adjuvants exhibit particularly good electrolyte tolerance and are stable to hard water when used in combination with fertilizers.

46 Claims, No Drawings

US 6,432,884 B1

AGRICULTURAL ADJUVANT

CROSS-REFERENCE TO RELATED APPLICATIONS

This application is a continuation-in-Dart of application Ser. No. 08/986,493, filed on 12/08/97 now abandoned the entire contents of which are incorporated herein by reference.

STATEMENT REGARDING FEDERALLY SPONSORED RESEARCH OR DEVELOPMENT

Not Applicable.

BACKGROUND OF THE INVENTION

The present invention generally relates to agricultural adjuvants. It is known that various pesticides such as insecticides, insect repellents, fungicides, bactericides, herbicides, and plant growth regulators may be formulated into various agricultural products for use on crops and ornamental plants, for controlling weeds, insects and the like. These products may be applied in the form of a liquid or a semi-solid dispersion.

The successful employment of any pesticide depends upon its proper formulation in a preparation that can be easily combined with water into ready-to-use form for application onto an agricultural substrate with safety to the applicator, animals and plants. The preparation and use of such formulations typically necessitates making them in concentrated form. Thus, the use of auxiliary agents such as solvents, emulsifiers, wetting and dispersing agents are typically required. The preparation of such pesticide concentrates, however, often times poses certain formulation problems due to the incompatibility of the pesticide component with other components combined therewith such as electrolytes, hard water and fertilizers.

BRIEF SUMMARY OF THE INVENTION

Compositions have been discovered which are useful as adjuvants for agricultural chemical formulations containing herbicides, growth regulator, crop desiccants, defoliants which exhibit particularly good electrolyte tolerance and are stable to hard water and/or when used in combination with fertilizers. The compositions according to the present invention are comprised of a lower alkanol ester of a fatty acid and an emulsifier package. The emulsifier package is comprised of an nonionic surfactant selected from the group consisting of an ethoxylated castor oil, an alkoxylated castor oil, an ethylene-propylene block copolymer, an ethoxylated-propoxylated alkyl phenol, an ethoxylated sorbitan fatty acid ester, a sorbitan fatty acid ester and an anionic surfactant selected from the group consisting of an ethoxylated partial phosphate ester, alkyl sulfate, an alkyl ether sulfate, a branched alkyl benzene sulfonate, a linear alkyl benzene sulfonate and an alpha olefin sulfonate.

BRIEF DESCRIPTION OF THE SEVERAL VIEWS OF THE DRAWING

Not Applicable.

DETAILED DESCRIPTION OF THE INVENTION:

The term target substrate, as used herein, means a plant, a plant pest, or a combination of a plant and a plant pest. A plant pest is defined as any living stage of any weed, insects, mites, nematodes, slugs, snails, protozoa, or other invertebrate animals, bacteria, fungi, other parasitic plants or reproductive parts thereof, viruses, or any organisms similar to or allied with any of the foregoing, or any infectious substances which can directly or indirectly injure or cause disease or damage in any plants or parts thereof, or any processed, manufactured, or other products of plants.

The adjuvant of the present invention is comprised of two primary components: (1) one or more lower alkanol fatty acid esters and, (2) an emulsifier package. The lower alkanol ester of a fatty acid is any saturated or unsaturated fatty acid having from about 6 to about 22 carbon atoms such as caproic acid, caprylic acid, pelargonic acid, palmitic acid, stearic acid and, oleic acid esterified with a $C_{1-4}$ alcohol such as methanol, ethanol, propanol and, butanol. Preferred lower alkanol esters of a fatty acid are ethyl canolate, ethyl rapeseedate or ethyl oleate.

The emulsifier package is comprised of a combination of one or more nonionic surfactants selected from the group consisting of an ethoxylated castor oil, an ethoxylated-propoxylated castor oil, an ethoxylated sorbitan fatty acid ester, an ethylene-propylene block copolymer, an ethoxylated-propoxylated alkyl phenol, a sorbitan fatty acid ester and one or more anionic surfactants selected from the group consisting of an ethoxylated partial phosphate ester, alkyl sulfate, an alkyl ether sulfate, a branched alkyl benzene sulfonate, a linear alkyl benzene sulfonate and an alpha olefin sulfonate. The preferred nonionic surfactants are ethoxylated sorbitan fatty acid esters and sorbitan fatty acid esters. Ethoxylated sorbitan fatty acid esters are sorbitol esterified with fatty acids having from about 6 to about 22 carbon atoms ethoxylated with from about 1 to about 30 moles of ethylene oxide (EO). The preferred sorbitan fatty acid esters are sorbitol esterified with fatty acids having from about 6 to about 22 carbon atoms. The most preferred nonionic surfactant is one which is a combination of sorbitan esters and ethoxylated sorbitan esters. A most preferred combination comprises from about 60% to about 95% by weight of ethoxylated sorbitan trioleate having a degree of ethoxylation of about 20 and from about 5% to about 40% by weight of sorbitan trioleate.

The anionic surfactants that can be used in the compositions according to the invention are selected from the group consisting of an ethoxylated partial phosphate ester, an alkyl sulfate and, an alkyl ether sulfate, a branched alkyl benzene sulfonate, a linear alkyl benzene sulfonate and an alpha olefin sulfonate. The preferred anionic surfactant is an ethoxylated partial phosphate ester. The ethoxylated partial phosphate esters are partial phosphate esters of polyoxyalkylene ethers. These partial esters are prepared by methods well known to those skilled in the art such as, for example, by reaction of a monofunctional polyoxyalkylene ether with phosphoric acid, diphosphorus pentoxide, polyphosphoric acid, or phosphorus oxytrichloride. These partial phosphate esters are described in U.S. Pat. No. 4,966,728 at column 3, lines 14–33, the contents of which are incorporated herein by reference. A preferred ethoxylated partial phosphate ester is phosphoric acid partially esterified with nonyl phenol (EO)-9, (nonyl phenol ethoxylated with 9 moles of ethylene oxide).

The alkyl sulfates that can be used in the compositions according to the invention are those wherein the alkyl group has from about 6 to about 22 carbon atoms. The alkyl ether sulfates that can be used in the compositions according to the invention are those wherein the alkyl group has from about 6 to about 22 carbon atoms. The branched alkyl benzene sulfonates that can be used in the compositions according to the invention are those wherein the alkyl group can be branched and has from about 6 to about 22 carbon atoms. The linear alkyl benzene sulfonates that can be used in the compositions according to the invention are those wherein the alkyl group is an essentially unbranched alkyl group having from about 6 to about 22 carbon atoms. The alpha olefin sulfonates that can be used in the compositions according to the invention are those wherein the alkyl group has from about 6 to about 22 carbon atoms.

A preferred adjuvant composition according to the invention is (1) from about 50% to about 95% by weight of a lower alkanol ester-of a fatty acid and (2) from about 5% to about 50% by weight of an emulsifier package wherein the emulsifier package is comprised of: (a) from about 50% to about 94% by weight of the emulsifier package of an ethoxylated sorbitan fatty acid ester having from 1 to 30 moles of EO; (b) from about 1% to about 20% by weight of the emulsifier package of a sorbitan fatty acid ester; (c) from about 5% to about 35% by weight of the emulsifier package of an ethoxylated partial phosphate ester. A particularly preferred composition is comprised of 75% ethyl canolate (oleate) and 25% of an emulsifier package which contains 80% of a (90/10) blend of POE (20) sorbitan trioleate and sorbitan trioleate and 20% of phosphoric acid partially esterified with nonyl phenol (EO)-9. A most preferred composition is comprised of from about 75% to about 76% of Ethyl Canolate; from about 16% to about 18% of POE(20) Sorbitan Trioleate; from about 1 % to about 2% of Sorbitan Trioleate; from about 4% to about 5% of phosphoric acid partially esterified with nonyl phenol (EO)-9.

The pH of the adjuvant compositions according to the invention (1% solution in distilled water) can range from about 4.0 to about 7.0 with the preferred range being from about 5.5 to about 6.5 for pH sensitive pesticides which may hydrolyze such as sulfonyl urea type products. The pH can be adjusted with any suitable base such as monoethanolamine, triethanolamine, KOH, NaOH, and the like.

The compositions according to the invention can be made by simply mixing the ingredients together.

According to another aspect of the present invention, there is provided a pesticide composition for use in treating target substrates such as those disclosed previously. The pesticide composition is generally comprised of the above-disclosed adjuvant composition and an effective amount of a biologically active ingredient. The biologically-active ingredients that can be used in the pesticide compositions according to the invention are generally selected from the group consisting of insecticides, insect repellents, fungicides, bactericides, bacteriostats, herbicides, crop dessicants, defoliants and plant growth regulators. Suitable insecticides include, but are not limited to, O,O-diethyl O-(2-isopropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl) phosphorodithioate, O,O-dimethyl-S-(N-methyl-N-formylcarbamoylmethyl)phosphorodithioate, O,O-dimethyl S-2-[(ethylthio)ethyl]phosphorodithioate, O,O-diethyl Insect repellents which may be employed include but are not limited to 2-ethyl-1,3-hexanediol; N-octyl bicycloheptene dicarboximide; N,N-diethyl-M-toluamide; 2,3:4,5-Bis (2-butylene) tetrahydro-2-furaldehyde; Di-n-propyl isocinchomeronate; and 2-hydroxyethyl-n-octyl sulfide.

Fungicides which may be employed include but are not limited to 3,3'-ethylenebis (tetrahydro-4,6-dimethyl-2H-1,3, 5-thiadiazine-2-thione), zinc or manganese ethylenebis (dithiocarbamate), bis-(dimethyidithiocarbamoyl)disulfide, zinc propylenebis (dithiocarbamate), bis (dimethyldithiocarbamoyl) ethylenediamine; nickel dimethyldithiocarbamate, methyl-1 (butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10, 11-dehydrodibenzo (b,f)azepine; pyridine fungicides such as zinc bis(1-hydroxy-2(1H) pyridinethionate and 2-pyridinethiol-1-oxide sodium salt; O,O-diisopropyl S-benzylphosphorothioate and O-ethyl S,S-diphenyldithiophosphate; phthalimide fungicides such as N-(2,6-p-diethylphenyl)phthalimide and N-(2,6-diethylphenyl)-4-methylphthalimide; dicarboxyimide fungicides such as N-trichloromethylthio 4-cyclohexene-1,2-dicarboxyimide and N-tetrachloroethylthio-4-cyclohexene-1,2-dicarboxyimide; 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate, pentachloronitrobenzene; 1,4-dichloro-2,5-dimethoxybenzene; 5-methyl-s-triazol-(3, 4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1,2,4-thiazole; 2,4-dichloro6-(O-chloroanilino)-1,3,5-triazine; 2,3-dicyano-1,4-dithioanthraquinone; copper 8-quinolinate; polyoxine; S-2-[(ethylthio)ethyl]phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphorothioate, O,O-dimethyl-O-)3-methyl-4-methylmercaptophenyl) thiophosphate, O-ethyl O-p-cyanophenyl-O-phenylphosphorothioate, O,O-dimethyl-S-(1,2-dicarboethoxyethyl) phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl]O,O-diethyl phosphorodithioate, 2-chloro-1-(2,4-dichlorophenyl)vinyl diethylphosphate O,O-diethyl O-(3-oxo-2-phenyl-2 H-pyridazine6-yl) phosphorothioate, O,O-dimethyl S-(1-methyl-2-ethylsulfinyl)-ethyl phosphorothiolate, O,O-dimethyl S-phthalimidomethyl phosphorodithioate, O,O-diethyl 2,2, 2-trichloroethanol, 2-(p-tert-butyl-phenoxy)isopropyl-2'-chloroethylsulfite, azoxybenzene, di(p-chlorophenyl)-cyclopropyl carbinol, di[tri(2,2-dimethyl-2-phenylethyl)tin] oxide, 1-(4-chlorophenyl)-3-(2,6-difluorobenzoyl)urea and S-tricyclohexyltin O,O-diisopropylphosphorodithioate; 2-methyl-2-(methylthio)propionaldehyde O-(methylcarbamoyl)oxime; ethyl [2-(4-phenoxyphenoxy) ethyl] carbamate; butyl-2,3-dihydro-2,2-dimethylbenzofuran-7-yl N,N'-dimethyl-N,N'-thiodicarbamate; 1-naphthyl methyl carbamate; 2-(ethylthiomethyl)phenyl methylcarbamate; 5-(4-phenoxybutyl)dimethylthiocarbamate; dimethyl N,N' (thiobis(methylimino)carbonyloxy)-bis(ethanimidothioate); (RS)-α-cyano-3-phenoxybenzyl-(RS)-2-(4-chlorophenyl)-3-methylbutyrate; (RS)-α-cyano-3-phenoxyphenyl-(RS)-2, 2-dichloro-1-(4-ethoxyphenyl)cyclopropanecarboxylate; (RS)-α-acyano-3-phenoxybenzyl-N-(2-chloro-α,α,α-- trifluoro-p-tolyl-D-valinate; 3-phenoxybenzyl-(1RS)-cis, trans-3-(2,2-dichlorovinyl)-2,2-dimethylcyclopropanedicarboxylate. validamycin; cycloheximide; iron methanearsonate; diisopropyl 1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazol-1-yl)-2-butanone; methyl-D,L-N-(2,6-dimethylphenyl)-N-(2'-methoxyacetyl) alaninate; N-propyl-N-[2-(2,4,6-trichlorophenoxy)ethyl]imidazol-1-carboxamide; N-(3,5-dichlorophenyl)succinamide; tetrachloroisophthalonitrile; 2-dimethylamino-4-methyl-5-n-butyl-4-hydroxypyrimidine; 2,6-dichloro-4-nitroaniline; 3-methyl-4-chlorobenzthiazol-2-one; 1,2,5,6-tetrahydro-4H-pyrrolol-[3,2,1-i,j]quinoline-2-one; 3'-isopropoxy-2-methylbenzanilide; 1-[2-(2,4-dichlorophenyl)-4-ethyl-1,3-dioxorane-2-methyl]-1H,1,2,4-triazol; 1,2-benzisothiazoline-3-one; basic copper chloride; basic copper sulfate; N'-dichlorofluoromethylthio-N,N-dimethyl-N-phenyl sulfamide; ethyl-N-(3-dimethylaminopropyl) thiocarbamate hydrochloride; piomycin; S,S-6-methylquinoxaline-2,3-di-yldithiocarbonate; complex of zinc and manneb; di-zinc bis(dimethyldithiocarbamate) ethylenebis (dithiocarbamate).

Plant growth regulators which may be employed include but are not limited to N-methoxycarbonyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; triazine herbicides such as 2-methylthio-4,6-bisethylamino-1,3,5-triazine, 2-chloro-4,6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis(isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof. 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether,2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl) carbamate, isopropyl-N-(3-chlorophenyl)carbamate and methyl-N-(3,4'-dichlorophenyl)carbamate; uracil herbicides such as 5-bromo-3-sec-butyl-methyluracil and 1-cyclohexyl-3,5-propyleneuracil; thiolcarbamate herbicides such as S-(4-chlorobenzyl)-N,N-diethylthiolcarbamate,S-ethyl-N-cyclohexyl-N-ethylthiolcarbamate and S-ethyl-hexahydro-1H-azepine-1-carbothioate and S-ethyl-N,N-di-n-propyl-thiocarbamate; pyridinium herbicides such as 1,1'-di-methyl-4,4'-bispyridinium dichloride; phosphoric herbicides such as N-(phosphonomethyl)glycine; aniline herbicides such as alpha-trifluoro-2,6-dinitro-N,N-dipropyl-p-toluidine, 4-(methylsulfonyl)-2,6-dinitro-N,N-dipropylaniline and N[3], N[3]-diethyl-2,4-dinitro6-trifluoromethyl-1,3-phenylene diamine; acid anilide herbicides such as 2-chloro-2',6'-diethyl-N-(butoxymethyl)acetoanilide, 2-chloro-2',6'-diethyl-N-(methoxymethyl)acetoanilide, and 3,4-dichloropropionanilide; pyrazole herbicides such as 1,3-dimethyl-4-(2,4-dichlorobenzoyl)-5-hydroxypyrazole and 1,3-di-methyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl, N-(4-chlorophenyl)carbamoyl]4-chloro-5-methyl-4-isooxazoline-3-one; 3-isopropylbenzo-2-thia-1,3-diazinone-(4)-2,4-dioxide and 3-(2-methyl-phenoxy) pyridazine.

According to yet another aspect of the present invention, there is provided a process for treating a target substrate which involves contacting the substrate with the above-disclosed aqueous pesticide composition thereby killing a pest or arresting the growth of a pest. The pesticide composition may be applied by aerial spraying, by in-seed row application, with a fertilizer or the like.

It should be noted that additional solvents, emulsifiers and adjuvants may be used by the applicator, if desired. It is thus within the skill of the applicator to determine if, and in what amounts, additional ingredients will be employed.

The following examples are meant to illustrate but not to limit the invention.

EXAMPLE 1

A composition according to the invention is comprised of: (weight %) 75% Ethyl Canolate (Rapeseedate); 18% EMSORB® 6913 POE(20) Sorbitan Trioleate; 2% EMSORB® 2503 Sorbitan Trioleate; 5% POE(9) Nonylphenol Phosphate Ester, Free Acid; QS Monoethanolamine, KOH, etc. to adjust pH (1% solution in distilled water) to 4.0 to 7.0.

EXAMPLE 2

A composition according to the invention is comprised of: (weight %) 76% Ethyl Canolate (Rapeseedate); 16.6% EMSORB® 6913 POE(20) Sorbitan Trioleate; 1.9% EMSORB® 2503 Sorbitan Trioleate; 4.6% POE(9) Nonylphenol Phosphate Ester, Free Acid; QS Triethanolamine to adjust pH (1% solution in distilled water) to 4.5 to 5.5.

What is claimed is:

1. A composition comprising: (1) from about 50 to about 95% by weight of a lower alkanol ester of a fatty acid and, (2) from about 5 to about 50% by weight of an emulsifier package wherein said emulsifier package is comprised of (a) a nonionic surfactant selected from the group consisting of an ethoxylated castor oil, an ethoxylated-propoxylated castor oil, an ethylene-propylene block copolymer, an ethoxylated-propoxylated alkyl phenol, an ethoxylated sorbitan fatty acid ester, a sorbitan fatty acid ester and combinations thereof and, (b) an anionic surfactant selected from the group consisting of an ethoxylated partial phosphate ester, alkyl sulfate, an alkyl ether sulfate, a branched alkyl benzene sulfonate, a linear alkyl benzene sulfonate, an alpha olefin sulfonate and combinations thereof.

2. The composition of claim 1 wherein said lower alkanol ester of a fatty acid is a $C_{1-4}$ ester.

3. The composition of claim 1 wherein said lower alkanol ester of a fatty acid is a $C_{1-4}$ ester of a fatty acid having from about 6 to about 22 carbon atoms.

4. The composition of claim 1 wherein said lower alkanol ester of a fatty acid is ethyl canolate, ethyl rapeseedate or ethyl oleate.

5. The composition of claim 1 wherein said nonionic surfactant is a combination of an ethoxylated sorbitan fatty acid ester and a sorbitan fatty acid ester.

6. The composition of claim 1 wherein said nonionic surfactant is a combination comprised of from about 60% to about 95% by weight of ethoxylated sorbitan trioleate having a degree of ethoxylation of about 20 and from about 5% to about 40% by weight of sorbitan trioleate.

7. The composition of claim 1 wherein said anionic surfactant is an ethoxylated partial phosphate ester.

8. The composition of claim 7 wherein said anionic surfactant is a phosphoric acid partially esterified with nonyl phenol (EO)-9.

9. A composition comprised of: (1) from about 50% to about 95% by weight of a lower alkanol ester of a fatty acid and (2) from about 5% to about 50% by weight of an emulsifier package wherein the emulsifier package is comprised of: (a) from about 50% to about 94% by weight of the emulsifier package of an ethoxylated sorbitan fatty acid ester having from 1 to 30 moles of EO; (b) from about 1% to about 20% by weight of the emulsifier package of a sorbitan fatty acid ester; (c) from about 5% to about 35% by weight of the emulsifier package of an ethoxylated partial phosphate ester.

10. The composition of claim 9 wherein said lower alkanol ester of a fatty acid is a $C_{1-4}$ ester.

11. The composition of claim 9 wherein said lower alkanol ester of a fatty acid is a $C_{1-4}$ ester of a fatty acid having from about 6 to about 22 carbon atoms.

12. The composition of claim 9 wherein said lower alkanol ester of a fatty acid is ethyl canolate, ethyl rapeseedate or ethyl oleate.

13. The composition of claim 12 wherein said lower alkanol ester of a fatty acid is ethyl canolate.

14. The composition of claim 9 wherein said anionic surfactant is an ethoxylated partial phosphate ester.

15. The composition of claim 14 wherein said anionic surfactant is a phosphoric acid partially esterified with nonyl phenol (EO)-9.

16. A composition comprised of from about 75% to about 76% of Ethyl Canolate; from about 16% to about 18% of POE(20) Sorbitan Trioleate; from about 1% to about 2% of Sorbitan Trioleate; from about 4% to about 5% of phosphoric acid partially esterified with nonyl phenol (EO)-9.

17. A composition which is the product of the process which comprises mixing: (1) from about 5 to about 95% by weight of a lower alkanol ester of a fatty acid and, (2) from about 5 to about 50% by weight of an emulsifier package wherein said emulsifier package is comprised of (a) a nonionic surfactant selected from the group consisting of an ethoxylated castor oil, an ethoxylated-propoxylated castor oil, an ethylene-propylene block copolymer, an ethoxylated-propoxylated alkyl phenol, an ethoxylated sorbitan fatty acid ester, a sorbitan fatty acid ester and combinations thereof and, (b) an anionic surfactant selected from the group consisting of an ethoxylated partial phosphate ester, alkyl sulfate, an alkyl ether sulfate, a branched alkyl benzene sulfonate, a linear alkyl benzene sulfonate, an alpha olefin sulfonate and combination thereof.

18. The composition of claim 17 wherein said lower alkanol ester of a fatty acid is a $C_{1-4}$ ester.

19. The composition of claim 17 wherein said lower alkanol ester of a fatty acid is a $C_{1-4}$ ester of a fatty acid having from about 6 to about 22 carbon atoms.

20. The composition of claim 17 wherein said lower alkanol ester of a fatty acid is ethyl canolate, ethyl rapeseedate or ethyl oleate.

21. The composition of claim 17 wherein said nonionic surfactant is a combination of an ethoxylated sorbitan fatty acid ester and a sorbitan fatty acid ester.

22. The composition of claim 17 wherein said nonionic surfactant is a combination comprised of from about 60% to about 95% by weight of ethoxylated sorbitan trioleate having a degree of ethoxylation of about 20 and from about 5% to about 40% by weight of sorbitan trioleate.

23. The composition of claim 17 wherein said anionic surfactant is an ethoxylated partial phosphate ester.

24. The composition of claim 23 wherein said anionic surfactant is a phosphoric acid partially esterified with nonyl phenol (EO)-9.

25. A pesticide composition comprisead of an effective amount of a biologically active ingredient and a composition comprised of: (1) from about 50 to about 95% by weight of a lower alkanol ester of a fatty acid and, (2) from about 5 to about 50% by weight of an emulsifier package wherein said emulsifier package is comprised of (a) a nonionic surfactant selected from the group consisting of an ethoxylated castor oil, an ethoxylated-propoxylated castor oil, an ethylene-propylene block copolymer, an ethoxylated-propoxylated alkyl phenol, an ethoxylated sorbitan fatty acid ester, a sorbitan fatty acid ester and combinations thereof and, (b) an anionic surfactant selected from the group consisting of an ethoxylated partial phosphate ester, alkyl sulfate, an alkyl ether sulfate, a branched alkyl benzene sulfonate, a linear alkyl benzene sulfonate, an alpha olefin sulfonate and combinations thereof.

26. The pesticide composition of claim 25 wherein said biologically active ingredient is selected from the group consisting of an insecticide, an insect repellent, a fungicide, a bactericide, a bacteriostat, a herbicide, a crop dessicant, a defoliant, and a plant growth regulator.

27. The pesticide composition of claim 26 wherein said biologically active ingredient is a herbicide.

28. The pesticide composition of claim 25 wherein said lower alkanol ester of a fatty acid is a $C_{1-4}$ ester.

29. The pesticide composition of claim/25 wherein said lower alkanol ester of a fatty acid is a $C_{1-4}$ ester of a fatty acid having from about 6 to about 22 carbon atoms.

30. The pesticide composition of claim 25 wherein said lower alkanol ester of a fatty acid is ethyl canolate, ethyl rapeseedate or ethyl oleate.

31. The pesticide composition of claim 25 wherein said nonionic surfactant is a combination of an ethoxylated sorbitan fatty acid ester and a sorbitan fatty acid ester.

32. The pesticide composition of claim 25 wherein said nonionic surfactant is a combination comprised of from about 60% to about 95% by weight of ethoxylated sorbitan trioleate having a degree of ethoxylation of about 20 and from about 5% to about 40% by weight of sorbitan trioleate.

33. The pesticide composition of claim 25 wherein said anionic surfactant is an ethoxylated partial phosphate ester.

34. The pesticide composition of claim 33 wherein said anionic surfactant is a phosphoric acid partially esterified with nonyl phenol (EO)-9.

35. A pesticide composition comprised of an effective amount of a biologically active ingredient and a composition comprised of from about 75% to about 76% of ethyl canolate; from about 16% to about 18% of POE(20) sorbitan trioleate; from about 1% to about 2% of sorbitan trioleate; from about 4% to about 5% of phosphoric acid partially esterified with nonyl phenol (EO)-9.

36. A process for treating a target substrate comprising contacting said substrate with a pesticide composition comprised of an effective amount of a biologically active ingredient and a composition comprised of: (1) from about 50 to about 95% by weight of a lower alkanol ester of a fatty acid and, (2) from about 5 to about 50% by weight of an emulsifier package wherein said emulsifier package is comprised of (a) a nonionic surfactant selected from the group consisting of an ethoxylated castor oil, an ethoxylated-propoxylated castor oil, an ethylene propylene block copolymer, an ethoxylated-propoxylated alkyl phenol, an ethoxylated sorbitan fatty acid ester, a sorbitan fatty acid ester and combinations thereof and, (b) an anionic surfactant selected from the group consisting of an ethoxylated partial phosphate ester, alkyl sulfate, an alkyl ether sulfate, a branched alkyl benzene sulfonate, a linear alkyl benzene sulfonate, an alpha olefin sulfonate and combinations thereof.

37. The process of claim 36 wherein said biologically active ingredient is selected from the group consisting of an insecticide, an insect repellent, a fungicide, a bactericide, a bacteriostat, a herbicide, a crop dessicant, a defoliant, and a plant growth regulator.

38. The process of claim 37 wherein said biologically active ingredient is a herbicide.

39. The process of claim 36 wherein said lower alkanol ester of a fatty acid is a $C_{1-4}$ ester.

40. The process of claim 36 wherein said lower alkanol ester of a fatty acid is a $C_{1-4}$ ester of a fatty acid having from about 6 to about 22 carbon atoms.

41. The process of claim 36 wherein said lower alkanol ester of a fatty acid is ethyl canolate, ethyl rapeseedate or ethyl oleate.

42. The process of claim 36 wherein said nonionic surfactant is a combination of an ethoxylated sorbitan fatty acid ester and a sorbitan fatty acid ester.

43. The process of claim 36 wherein said nonionic surfactant is a combination comprised of from about 60% to about 95% by weight of ethoxylated sorbitan trioleate having a degree of ethoxylation of about 20 and from about 5% to about 40% by weight of sorbitan trioleate.

44. The process of claim 36 wherein said anionic surfactant is an ethoxylated partial phosphate ester.

45. The pesticide composition of claim 44 wherein said anionic surfactant is a phosphoric acid partially esterified with nonyl phenol (EO)-9.

46. A process for treating a target substrate comprising contacting said substrate with a pesticide composition comprised of an effective amount of a biologically active ingredient and a composition comprised of from about 75% to about 76% of ethyl canolate; from about 16% to about 18% of POE(20) sorbitan trioleate; from about 1% to about 2% of sorbitan trioleate; from about 4% to about 5% of phosphoric acid partially esterified with nonyl phenol (EO)-9.

\* \* \* \* \*